US00PP30577P2

(12) United States Plant Patent
Vitten et al.

(10) Patent No.: US PP30,577 P2
(45) Date of Patent: Jun. 18, 2019

(54) RASPBERRY PLANT VARIETY NAMED 'DRISRASPTWELVE'

(50) Latin Name: ***Rubus idaeus* L.**
Varietal Denomination: DrisRaspTwelve

(71) Applicant: Driscoll's, Inc., Watsonville, CA (US)

(72) Inventors: Matthias D. Vitten, Aptos, CA (US); Richard E. Harrison, Aptos, CA (US); Luis Miguel Rodriguez Martinez, Watsonville, CA (US)

(73) Assignee: Driscoll's, Inc, Watsonville, CA (US)

( * ) Notice: Subject to any disclaimer, the term of this patent is extended or adjusted under 35 U.S.C. 154(b) by 0 days.

(21) Appl. No.: 15/732,501

(22) Filed: Nov. 20, 2017

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP7,528 | P | 5/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| PP27,644 | P3 | 2/2017 | Hamilton et al. |
| PP28,775 | P2 | 12/2017 | Hamilton et al. |
| 2017/0311501 | P1 | 10/2017 | Vitton et al. |

OTHER PUBLICATIONS

Cousineau et al., "Use of Isoenzyme Analysis to Characterize Raspberry Cultivars and Detect Cultivar Mislabeling", HortScience vol. 27, No. 9, Sep. 1992, pp. 1023-1025.
Williams et al., "DNA Polymorphisms Amplified by Arbitrary Primers are Useful as Genetic Markers", Nucleic Acids Research, vol. 18, No. 22, 1990, pp. 6531-6535.
Unpublished U.S. Appl. No. 15/731,419, filed Jun. 6, 2017, titled "Raspberry Plant Variety Named 'Drisraspthirteen'".

*Primary Examiner* — Keith O. Robinson
(74) *Attorney, Agent, or Firm* — Morrison and Foerster LLP

(57) ABSTRACT

A new and distinct variety of raspberry plant named 'DrisRaspTwelve', particularly characterized by fruit that is sweet and large in size, and having improved fruit shelf-life, is disclosed.

4 Drawing Sheets

Latin name:
Botanical classification: *Rubus idaeus* L.
Varietal denomination: The varietal denomination of the claimed variety of raspberry plant is 'DrisRaspTwelve'.

BACKGROUND OF THE INVENTION

Raspberries are the edible fruit of a multitude of plant species in the genus *Rubus* of the rose family. Most raspberry species are in the subgenus *Idaeobatus*. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L), which has been denominated as 'DrisRaspTwelve'.

Raspberry plant variety 'DrisRaspTwelve' was discovered in Santa Cruz County, Calif. in August of 2011 and originated from a cross between the proprietary female parent raspberry plant 'RB608.1' (unpatented) and the proprietary male parent raspberry plant 'RD150.1' (unpatented). The original seedling of the new variety was asexually propagated at a nursery in Santa Cruz County, Calif.

'DrisRaspTwelve' was subsequently asexually propagated via tissue culture and root cuttings, and underwent further testing at a farm in Santa Cruz County, Calif. for five years (2011 to 2015). The present invention has been found to be stable and reproduce true to type through successive asexual propagations via tissue culture and root cuttings.

'DrisRaspTwelve' exhibits the following distinguishing characteristics when grown under normal horticultural practices in Santa Cruz County, Calif.:

1. Sweet flavor;
2. Large fruit size; and
3. Improved shelf-life and shipping qualities.

'DrisRaspTwelve' was selected for its sweet and large-sized fruit, and for improved fruit shelf-life.

BRIEF DESCRIPTION OF THE DRAWINGS

This new raspberry plant is illustrated by the accompanying photographs, which show fruit of the plant, as well as the primocanes, flowers, and leaves. The colors shown are as true as can be reasonably obtained by conventional photographic procedures. The photographs are of plants that are one year gold.

FIG. 1A shows the upper surface of plant leaves of variety 'DrisRaspTwelve'. FIG. 1B shows the lower surface of plant leaves of variety 'DrisRaspTwelve'.

DETAILED BOTANICAL DESCRIPTION

Figures 1A, 1B:
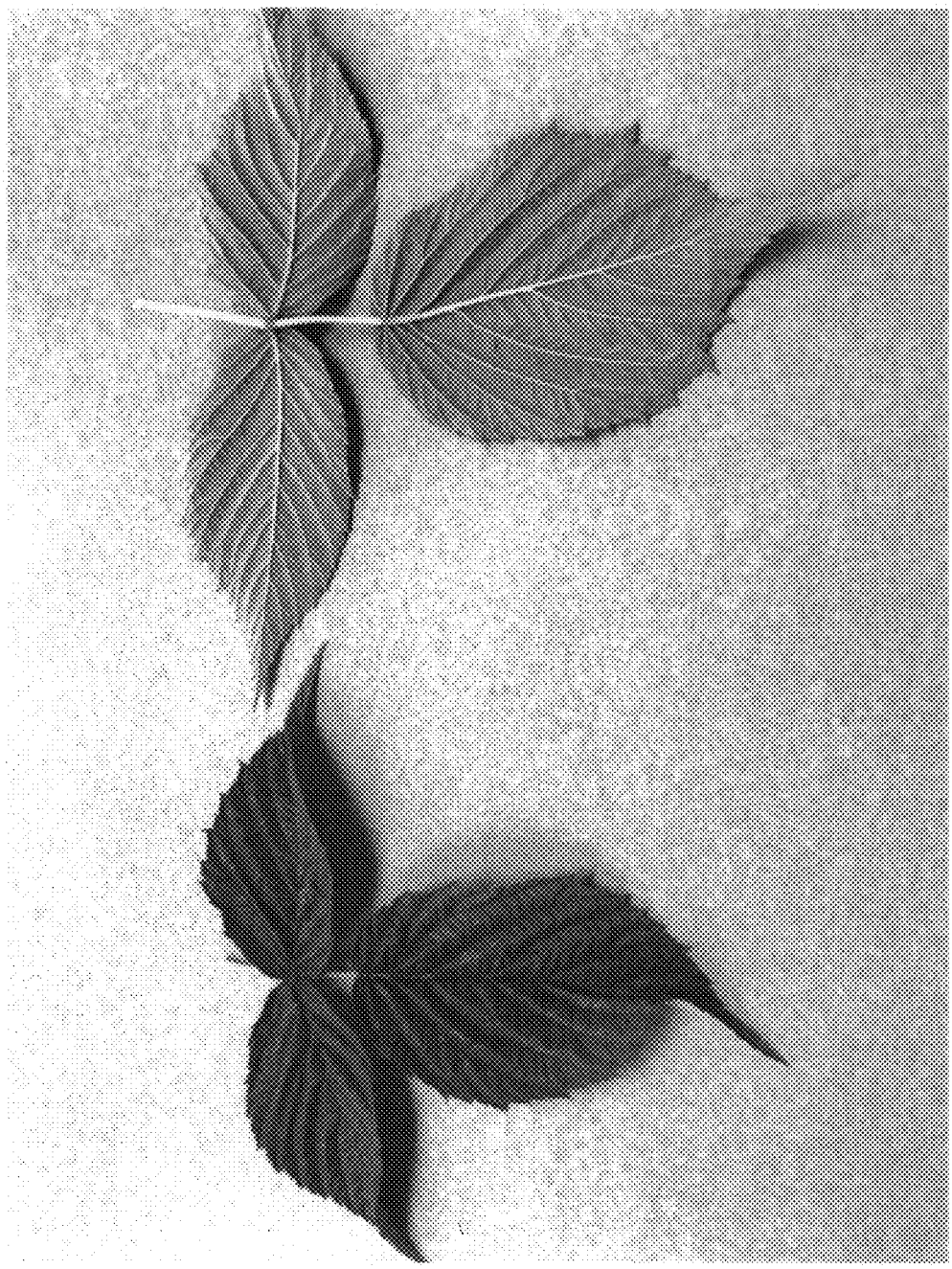
FIGS. 1A and 1B illustrate both the upper surface and the lower surface of plant leaves of variety 'DrisRaspTwelve'.
Figure 2:
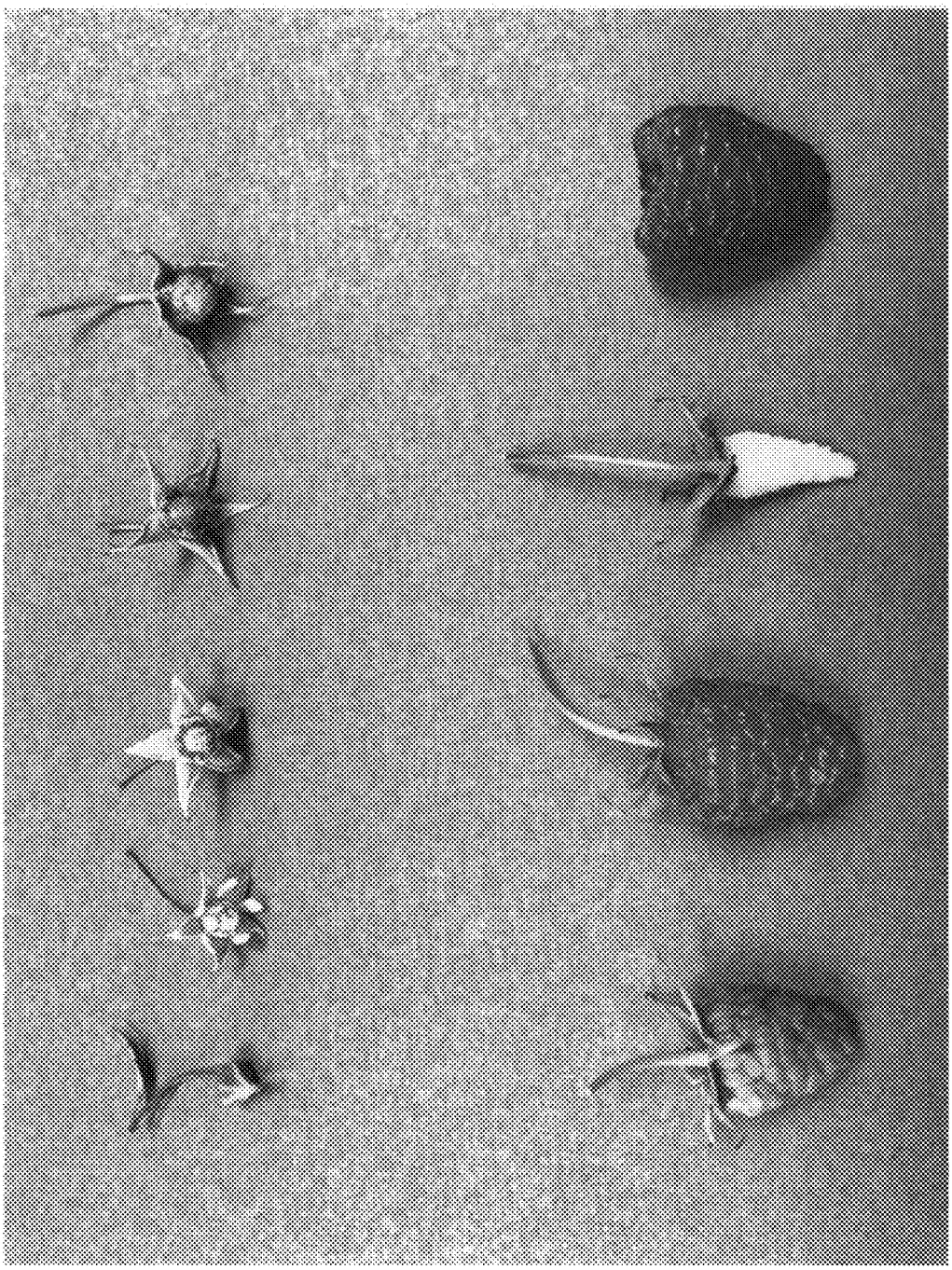
FIG. 2 illustrates typical flowers and fruit of variety 'DrisRaspTwelve' at various stages of development.
Figure 3:
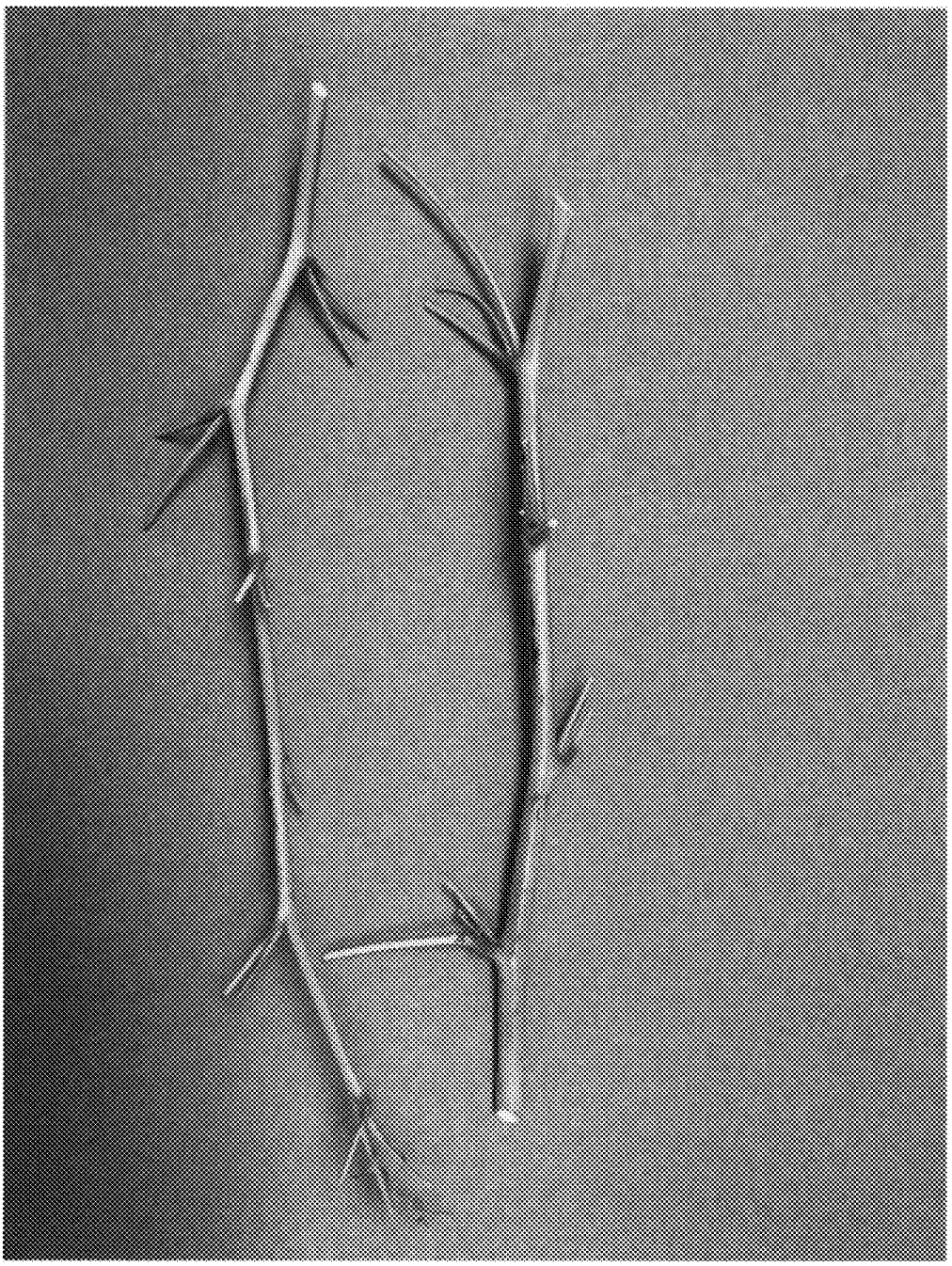
FIG. 3 illustrates canes of variety 'DrisRaspTwelve'.
Figure 4:
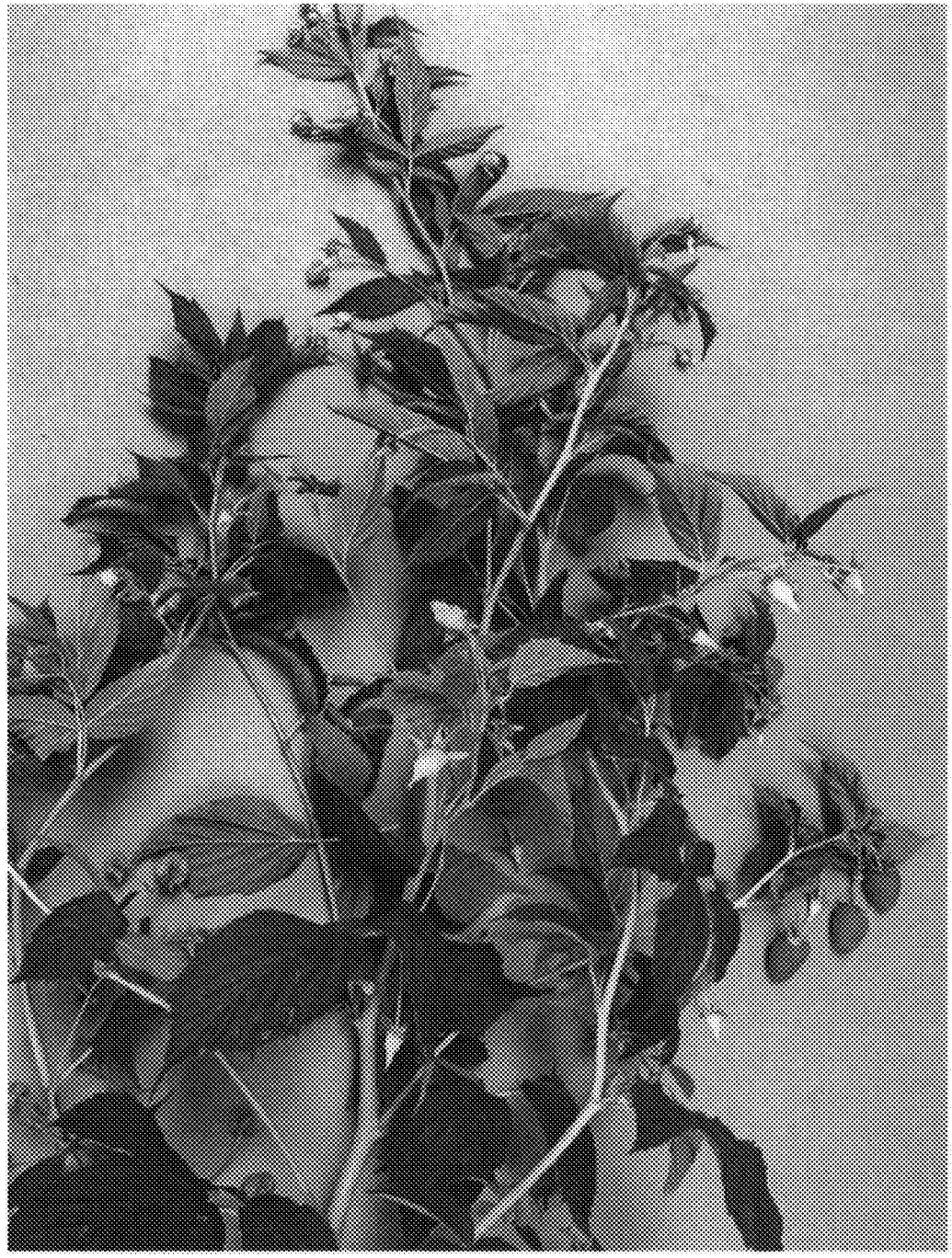
FIG. 4 illustrates a plant of variety 'DrisRaspTwelve'.

The following descriptions set forth the distinctive characteristics of 'DrisRaspTwelve'. The data that define these characteristics are based on observations taken in Santa Cruz County, Calif. from 2011 to 2015. This description is in accordance with UPOV terminology. Color designations, color descriptions, and other phenotypical descriptions may deviate from the stated values and descriptions depending upon variation in environmental, seasonal, climatic and cultural conditions. 'DrisRaspTwelve' has not been observed under all possible environmental conditions. The botanical description of 'DrisRaspTwelve' was taken from one-year-old plants. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family*.—Rosaceae.
*Botanical*.—*Rubus idaeus* L.
*Common name*.—Raspberry.
*Variety name*.—'DrisRaspTwelve'.

Parentage:

*Female parent*.—'RB608.1' (unpatented).
*Male parent*.—'RD150.1' (unpatented).

Plant:

*Propagation*.—Tissue culture and root cuttings.
*Height*.—188.3 cm.
*Width*.—158.5 cm.
*Length/width ratio*.—1.2.
*Self-fruitfulness*.—Self-fruitful.
*New cane growth habit*.—Semi-erect or semi-upright.

Primocanes:

*Cane length in autumn*.—130.6 cm.
*Internodal distance at central ⅓ of cane*.—8.25 cm.
*Anthocyanin coloration of cane*.—RHS 177B (Light reddish brown).
*Anthocyanin coloration of apex during rapid growth of very young shoot*.—Present.
*Intensity of anthocyanin coloration of apex during rapid growth of very young shoot*.—Medium.
*Percent of cane flowering as primocane*.—40%.
*Percent primocane yield of total yield*.—50%.
*Shape of cane cross section (from mid cane of primocane)*.—Rounded to angular.
*Pubescence on canes*.—Absent.

Floricanes:

*Dormant cane color in summer*.—RHS 175A (Moderate reddish brown).
*Fruiting lateral attitude in summer*.—Semi-erect.

Prickles (spines):

*Length at* 1.0 *m height at end of harvest season (from base to tip)*.—0.82 mm.
*Color (pigmentation)*.—RHS 138C (Moderate yellow green).
*Density on central third*.—Sparse.
*Attitude of tip*.—Upward.
*Presence and distribution on petioles*.—Absent.

Leaves:

*Terminal leaflet*.—Length: 143.2 mm. Width: 84.7 mm. Length/width ratio: 1.7. Leaf color: Green color of upper surface: RHS 135A (Dark green). Green color of lower surface: RHS 137C (Moderate yellow-green). Profile in cross section: Concave. Relief between veins (Rugosity): Medium. Overlapping or relative position of lateral leaflets: Free. Shape: Ovate. Apex: Complex. Base: Obtuse. Margin: Doubly serrate.

*Lateral leaflets* (*basal pair*).—Number of leaflets: Sometimes 3 and sometimes 5. Size: Length: 112.5 mm. Width: 60.1 mm. Length/width ratio: 1.9. Shape: Ovate. Apex: Complex. Base: Obtuse. Margin: Doubly serrate.

*Rachis length between terminal leaflet and adjacent lateral leaflets*.—27.8 mm.

*Petiole*.—Length: 0.6 mm. Diameter: 1.7 mm. Pigmentation of upper surface: RHS 138B (Moderate yellow-green). Pigmentation of underside: RHS 138A (Moderate yellowish green).

Stipules:

*Orientation*.—Erect.

Flowers:

*Diameter*.—32.07 mm.

*Petal length*.—9.74 mm.

*Petal width*.—4.39 mm.

*Length/width ratio*.—2.2.

*Petal color*.—RHS 143C (Strong yellow-green).

*Flowering period*.—Primocane: Late May to early June. Floricane: Late April to early May.

*Pedicel*.—Anthocyanin coloration: Present. Length: 53.4 mm. Diameter: 1.44 mm.

Fruit:

*Length*.—27.52 mm.

*Diameter*.—22.18 mm.

*Ratio of length to width*.—1.2.

*Average number of drupelets per fruit*.—90.

*Weight* (*g/fruit*).—Primocane: 5.5 g/fruit. Floricane: 5.2 g/fruit.

*Soluble solids* (*in brix*).—9.1%.

*Weight of seeds*.—0.002356 g/seed.

*Shape*.—Trapezoidal.

*Color*.—Immature fruit: RHS 139D (Moderate yellow-green). Maturing fruit: RHS 34C (Strong reddish orange). Mature fruit color: RHS 34C (Strong reddish orange).

*Firmness*.—Firm.

*Main bearing type*.—Both on previous year's cane in summer and on current year's cane in autumn.

*Harvest season*.—Time of ripening — primocane: Mid-Jung to late October. Time of ripening — floricane: Mid-April to mid-July.

*Yield*.—Primocane: 30,000 kg/ha to 35,000 kg/ha of marketable fruit per season from one-year-old plants when grown in Watsonville, Calif. Floricane: 35,000 kg/ha to 45,000 kg/ha of marketable fruit per season from one-year-old plants when grown in Watsonville, Calif.

COMPARISONS TO PARENTAL AND COMMERCIAL RASPBERRY VARIETIES

When 'DrisRaspTwelve' is compared to the female parent 'RB608.1' (unpatented), 'DrisRaspTwelve' produces fruit that is sweeter and larger in size than that of 'RB608.1'. Additionally, plants of 'DrisRaspTwelve' produce fruit that holds and ships better as compared to fruit produced by 'RB608.1' plants.

When 'DrisRaspTwelve' is compared to the male parent 'RD150.1' (unpatented), 'DrisRaspTwelve' produces fruit that is sweeter and larger in size than that of 'RD150.1'. Additionally, plants of 'DrisRaspTwelve' produce fruit that holds and ships better as compared to fruit produced by 'RD150.1' plants.

When 'DrisRaspTwelve' is compared to the commercial variety 'DrisRaspThree' (U.S. Plant Pat. No. 23,477), 'DrisRaspTwelve' produces fruit with a trapezoidal shape that is glossier and firmer than the fruit with an ovate (broad conical) shape produced by 'DrisRaspThree' plants. Additionally, 'DrisRaspTwelve' produces longer and broader terminal leaflets with a dark green color on the upper side, while 'DrisRaspThree' produces shorter and narrower terminal leaflets with a medium green color on the upper side. Moreover, 'DrisRaspTwelve' produces plants with a semi-upright growth habit, while 'DrisRaspThree' produces plants with an upright growth habit.

'DrisRaspTwelve' differs from the commercial variety 'Driscoll Maravilla' (U.S. Plant Pat. No. 14,804) in that 'DrisRaspTwelve' produces longer and broader terminal leaflets with a darker green color on the upper side than that of 'Driscoll Maravilla'. Additionally, 'DrisRaspTwelve' has free lateral leaflets, while 'Driscoll Maravilla' has overlapping lateral leaflets. Moreover, 'DrisRaspTwelve' produces fruit with a trapezoidal shape that has weak adherence to the receptacle, while 'Driscoll Maravilla' produces fruit with an ovate (broad conical) shape that has medium adherence to the receptacle.

What is claimed is:

1. A new and distinct variety of raspberry plant designated 'DrisRaspTwelve' as shown and described herein.

* * * * *